United States Patent [19]
Bolton

[11] Patent Number: 5,834,030
[45] Date of Patent: *Nov. 10, 1998

[54] METHOD OF INCREASING THE CONCENTRATION OF NITRIC OXIDE IN HUMAN BLOOD

[75] Inventor: Anthony E. Bolton, Sheffield, Great Britain

[73] Assignee: Vasogen, Inc., Ontario, Canada

[*] Notice: The term of this patent shall not extend beyond the expiration date of Pat. No. 5,591,457.

[21] Appl. No.: 477,818

[22] Filed: Jun. 7, 1995

Related U.S. Application Data

[63] Continuation-in-part of Ser. No. 941,326, Sep. 4, 1992, abandoned, which is a continuation-in-part of Ser. No. 832,798, Feb. 7, 1992, abandoned.

[51] Int. Cl.$^6$ .......................... A61K 33/00; A61K 35/14; A61K 41/00; A61L 2/10
[52] U.S. Cl. .......................... 424/613; 424/529; 424/718; 422/24; 422/44; 422/45; 422/46; 514/929; 435/2; 604/4; 604/20; 604/25
[58] Field of Search .................................... 424/613, 718, 424/529; 422/24, 45, 44, 46; 604/4, 20, 25; 250/493.1; 435/2; 514/929

[56] References Cited

U.S. PATENT DOCUMENTS

| | | | |
|---|---|---|---|
| 695,647 | 3/1902 | Smith | 604/25 |
| 3,715,430 | 2/1973 | Ryan | 424/127 |
| 4,632,980 | 12/1986 | Zee et al. | 530/380 |
| 4,831,268 | 5/1989 | Fisch et al. | 250/432 |
| 4,968,483 | 11/1990 | Muller et al. | 422/45 |
| 4,983,637 | 1/1991 | Herman | 514/724 |
| 5,052,382 | 10/1991 | Wainwright | 128/202 |
| 5,547,635 | 8/1996 | Duthie, Jr. | 422/24 |
| 5,591,457 | 1/1997 | Bolton | 424/613 |

FOREIGN PATENT DOCUMENTS 1 068 428  5/1957  Germany.

OTHER PUBLICATIONS

Snyder et al., "Biological Roles of Nitric Oxide", Scientific American, May 1992, pp. 68–77.
Bredt et al., "Cloned and Expressed Nitric Oxide Synthase Structurally Resembles Cytochrome P–450 Reductase", Nature, vol. 351, Jun. 1991, pp. 714–718.
Ozone: "Historical Review", published in Biomedical Technology Dec. 1991.
British Medical Journal, vol. 296, Jan. 1988, pp. 330–331 entitled "Secondary Prevention of Vascular Disease by Prolonged Antiplatelet Treatment".
Mueller Medical International Inc., Technical Report and Clinical Update, Shannon, et al., Oakville, Canada, Jun. 1990.
Chemical Abstracts 110: 121366, 1989.
Chemical Abstracts 122:38939, 1995.
Embase Abstract, Accession No. 1998031574, 1998.

*Primary Examiner*—John Pak
*Attorney, Agent, or Firm*—Nixon & Vanderhye

[57] ABSTRACT

A method of increasing the nitric oxide concentration in the blood of a human, which comprises: (a) contacting from about 0.01 ml to about 400 ml of blood with a nitric oxide concentration-increasing effective amount of ozone gas and ultraviolet radiation; and (b) administering the treated blood to a human. The method of the invention is useful for treating a variety of conditions benefitted by increased blood levels of nitric oxide.

12 Claims, No Drawings

METHOD OF INCREASING THE CONCENTRATION OF NITRIC OXIDE IN HUMAN BLOOD

CROSS-REFERENCE TO RELATED APPLICATIONS

This application is a continuation-in-part of U.S. patent application Ser. No. 07/941,326, filed on Sep. 4, 1992, now abandoned, the entire disclosure of which is incorporated herein by reference, which is in turn a continuation-in-part of U.S. patent application Ser. No. 07/832,798 (now abandoned) filed Feb. 7, 1992, the entire disclosure of which is incorporated herein by reference.

BACKGROUND OF THE INVENTION

1. Field of the Invention

This invention relates to methods of increasing the concentration of nitric oxide in human blood, and to methods of therapeutically treating human disease conditions associated with reduced in vivo blood levels of nitric oxide.

2. Description of the Prior Art

Platelets are the smallest of the formed elements of the blood. Every cubic millimeter of blood contains about 250 million platelets, as compared with only a few thousand white cells. There are about a trillion platelets in the blood of an average human adult. Platelets are not cells, but are fragments of the giant bone-marrow cells called megakaryocytes. When a megakaryocyte matures, its cytoplasm breaks up, forming several thousand platelets. Platelets lack DNA and have little ability to synthesize proteins. When released into the blood, they circulate and die in about 10 days. However, platelets do possess an active metabolism to supply their energy needs.

Because platelets contain a generous amount of contractile protein (actomyosin), they are prone to contract much as muscles do. This phenomenon explains the shrinkage of a fresh blood clot after it stands for only a few minutes. The shrinkage plays a role in forming a hemostatic plug when a blood vessel is cut. The primary function of platelets is that of forming blood clots. When a wound occurs, platelets are attracted to the site where they activate a substance (thrombin) which starts the clotting process. Thrombin, in addition to converting fibrinogen into fibrin, also makes the platelets sticky. Thus, when exposed to collagen and thrombin, the platelets aggregate to form a plug in the hole of an injured blood vessel.

Platelets not only tend to stick to one another, but to the walls of blood vessels as well. Because they promote clotting, platelets have a key role in the formation of thrombi. The dangerous consequences of thrombi are evident in many cardiovascular and cerebrovascular disorders.

The precise function of blood platelets in various human disease states has recently become increasingly understood as advances in biochemistry permit the etiologies of diseases to be better understood.

For example, many attempts have been made to explain the process of atherogenesis, that is, the creation of plaque which narrows arteries and, of particular concern, the coronary arteries. Recently, there has been increasing interest in the possible role of platelets in atherosclerosis.

In this regard, there is a growing body of evidence that nitric oxide (NO) in the blood exercises various biochemical functions. As the precise biological role of nitric oxide has been explored, it has become known that nitric oxide serves as an important messenger molecule in the brain and other parts of the body, governing diverse biological functions. In blood vessels, the principal endothelium-derived relaxing factor (EDRF) is believed to be nitric oxide, which stimulates vasodilation. Nitric oxide also inhibits platelet aggregation and is partially responsible for the cytotoxic actions of macrophages.

In the brain, nitric oxide mediates the actions of the excitatory neurotransmitter glutamate in stimulating cyclic GMP concentrations. Immunohistochemical studies have localized nitric oxide synthase (NOS) to particular neuronal populations in the brain and periphery. Inhibitors of nitric oxide synthase block physiological relaxation of the intestine induced by neuronal stimulation, indicating that nitric oxide has the properties of a neurotransmitter. In this regard, nitric oxide appears to be a novel type of neuronal messenger, in that, unlike conventional neurotransmitters, nitric oxide is not stored in synaptic vesicles and does not act on typical receptor proteins of synaptic membranes. One function of nitric oxide may be to protect neurons from ischemic and neurotoxic insults. See, Bredt et al., "Cloned and Expressed Nitric Oxide Synthase Structurally Resembles Cytochrome P-450 Reductase," Nature, Vol. 351, June, 1991, pages 714–718.

Thus, in addition to platelet aggregation associated diseases, a number of other disease states in humans are presently believed to be associated with inadequate nitric oxide levels in the blood. These nitric oxide associated conditions include: high blood pressure, neurological conditions such as depression, tumors, bacterial and fungal infections, and impotence.

It would therefore be desirable to provide a method for increasing the nitric oxide concentration in human blood, in order to treat the above-described human disease states which are characterized by nitric oxide deficiency.

A separate body of prior art discloses various methods of using ozone gas to treat certain human diseases, wounds and infections.

U.S. Pat. No. 695,657 to Smith discloses a portable ozonizer for the treatment of wounds. The device includes an ozonizer housed in a glass jacket, one end of which receives an air-supply tube and other end of which functions as an outlet tube for the ozonized air. The device enables topical application of ozone gas, which is said to be used to treat suppurating or gangrenous surfaces.

U.S. Pat. No. 3,715,430 to Ryan relates to a method and apparatus for producing substantially pure oxygen having a controlled content of ozone and higher oxygen polymers. The purified oxygen gas is exposed to ultraviolet light in a wavelength of 2485 to 2537 angstrom units in order to produce 5 to 500 parts per million of ozone and higher oxygen polymers in the gas mixture. Ryan indicates that the gas produced in this manner is non-irritating to the human body and may be intravenously injected into the blood stream for therapeutic use.

U.S. Pat. No. 4,632,980 to Zee et al. discloses a method of freeing blood and blood components of enveloped viruses by contacting the blood or blood product in an aqueous medium with an enveloped virus inactivating amount of ozone. The treatment is carried out at a temperature of 4° C. to 37° C., and an ozone concentration of 1–100 ppm. The disclosed process is said to useful for inactivating the hepatitis virus, HTLV-I, -II, and -III, and influenza virus.

U.S. Pat. No. 4,831,268 to Fisch et al. provides a method for the radiation of corporeal blood to prevent arteriosclerosis related heart and vascular diseases caused by disturbances in the fat exchange. The disclosed process involves irradiating the blood in a blood conducting tube with radiation having an intensity of from about 1 mWcm$^{-2}$ to 10 mWcm$^{-2}$ in a wavelength range of from about 320 nm to 600 nm.

U.S. Pat. No. 4,968,483 to Muller et al. discloses an apparatus for the production of oxygenated blood. The apparatus includes a vessel for containing the blood to be processed, an ultraviolet lamp and infrared lamp associated with the vessel, and a feed pipe extending into the vessel to a position near the bottom of the vessel, in which the feed pipe is connected to a source of ozone.

U.S. Pat. No. 4,983,637 to Herman relates to a method of treating systemic viral infections by the parenteral administration of pharmacologically effective amounts of ozonides of terpenes in pharmaceutically acceptable carriers. The disclosed method is particularly directed to the treatment of HIV infections.

U.S. Pat. No. 5,052,382 to Wainwright discloses an apparatus for the controlled generation and administration of ozone. The apparatus includes a generator for generating ozone, a monitor for monitoring the ozone production, a dosage device for providing a predetermined amount of ozone administration, and a computer control device for controlling the operation of the apparatus. The patent further discloses that administration of ozone to patients is known for the treatment of viral and bacterial infections, as well as for the treatment of external sores and wounds.

SUMMARY OF THE INVENTION

Applicant has unexpectedly discovered that in vitro nitric oxide concentrations in human blood may be raised by contacting from 0.01 ml to about 400 ml of blood with nitric oxide concentration-increasing effective amount of ozone gas and ultraviolet radiation.

The invention also contemplates a method of treating a condition in a human, by contacting from about 0.01 ml to about 400 ml of blood with nitric oxide concentration-increasing effective amount of ozone gas and ultraviolet radiation, followed by administration of the blood so treated to a human.

DESCRIPTION OF THE PREFERRED EMBODIMENTS

The present invention provides a method of increasing the nitric oxide concentration in the blood of a human, which comprises:

(a) contacting from about 0.01 ml to about 400 ml of blood with a nitric oxide concentration-increasing effective amount of ozone gas and ultraviolet radiation; and (b) administering the blood treated in step (a) to a human.

Examples 1 and 2 below show that an inhibition of blood platelet aggregation can only be achieved when the blood is treated with a combination of ozone gas and ultraviolet radiation (UV). Treatment of blood solely with ozone gas produces minimal inhibition of blood platelet aggregation. Treatment of blood solely with ultraviolet light produces no inhibition of platelet aggregation whatsoever. Moreover, Examples 3 and 4 show that the inhibition of blood platelet aggregation proceeds via a nitric oxide mediated mechanism, and that treatment of blood with ultraviolet light and ozone according to the invention increases nitric oxide concentrations in the blood. Example 5 shows that reinjection of such nitric oxide-enriched blood, so treated, into the human body enhances blood flow due to creation of a greater level of available nitric oxide in the blood vessels.

The combined treatment with ozone gas and ultraviolet light has therefore been unexpectedly found to produce a notable increase in the blood concentration of nitric oxide, which may be useful in treating a variety of disorders that are benefitted by increased blood levels of nitric oxide.

The ozone gas may be provided by any conventional source known in the art, such as an ozonizer. The ozone gas used in connection with the inventive method has a concentration of ozone of from about 0.5 to about 100 µg/ml. Preferably, the ozone gas has a concentration of from about 5 to about 50 µg/ml. The ozone gas is preferably delivered to the blood by means of a medical oxygen carrier, and is preferably contacted with the blood by any means known in the art, preferably by bubbling the ozone/oxygen mixture through the blood sample.

The ultraviolet radiation may be provided by any conventional source known in the art, for example by a plurality of low-pressure ultraviolet lamps. The invention preferably utilizes a standard UV-C source of ultraviolet radiation. Preferably employed are low-pressure ultraviolet lamps that generate a line spectrum wherein at least about 90% of the radiation has a wavelength of about 253.7 nm. It is believed that ultraviolet radiation having emission wavelengths corresponding to standard UV-A and UV-B sources would also provide acceptable results.

The blood to be treated with UV/ozone is preferably heated to a temperature of from about 0° to about 56° C. while being contacted with the ozone gas and ultraviolet radiation. Any suitable source of heat known in the art may be employed to heat the blood, preferably one or more infrared lamps. The blood may be heated to about 37°–43° C., most preferably about 42.5° C., prior to being contacted with the ozone gas and ultraviolet radiation. Preferably, the temperature of the blood is then maintained at about 42.5° C. during the treatment with UV/ozone.

Alternatively, the blood sample is heated while being subjected to UV radiation, until the blood reaches a predetermined temperature (preferably about 42.5° C.), at which point bubbling of ozone gas through the blood is commenced. The concurrent UV/ozone treatment is then maintained for a predetermined period of time, preferably about 3 minutes.

Another alternative method involves subjecting the blood to UV/ozone while heating the blood to a predetermined temperature (preferably about 42.5° C.), then either ending the treatment once the predetermined temperature is reached, or continuing UV/ozone treatment for a further period of time, most preferably about 3 minutes.

Heating the blood to about 42.5° C. with the infrared lamps preferably employed according to the invention has been found to take from about one minute and fifty seconds to about two minutes and ten seconds.

It will be understood that the source of blood treated according to the invention may be blood from an outside source, such as a blood donor of compatible blood type, which is treated with UV/ozone and then administered to a patient. Alternately, and preferably, the blood to be treated may be withdrawn from the human patient as an aliquot, treated with UV/ozone, then readministered to the patient from whom the aliquot of blood was taken. All or a portion of the blood removed from the patient may be treated and then readministered to the patient.

In general, from about 0.01 to about 400 ml of blood may be treated according to the invention. Preferred amounts are in the range of about 0.1 to 200 ml, and more preferably from about 1 to 50 ml of blood. The method most preferably involves treating about 10 ml of blood with ozone gas and ultraviolet radiation, then administering (or readministering) the treated blood to the patient by intramuscular injection.

Other conventional techniques known in the art for administering blood may be employed, such as inter-arterial injection, intravenous injection, subcutaneous injection, and intraperitoneal injection. The administration of small volumes of host blood in this fashion is termed micro-autohemotherapy.

The invention also contemplates an embodiment wherein blood is continuously removed from a patient's body and circulated through an apparatus which treats the blood with ozone gas and ultraviolet light as described above, before returning the blood to the patient. This procedure would have particular utility, for example, during the performance of operative procedures, such as coronary bypass surgery.

The blood is contacted with the ozone gas and ultraviolet radiation for a period of time sufficient to effectively raise the nitric oxide blood concentration in the patient. A treatment period of from about a few seconds to about 60 minutes, preferably from about 0.5 minutes to about 10 minutes, and most preferably about 3 minutes, has been found to provide satisfactory increase in nitric oxide blood levels. The blood is preferably maintained at a temperature of about 42.5° C. during the three minute treatment period.

The method should be carried out under sterile conditions known to those of ordinary skill in the art. The method of the invention may be carried out using conventional apparatus for ozonating blood and irradiating blood with ultraviolet radiation known to those skilled in the medical art. Preferably, an apparatus similar to that disclosed in U.S. Pat. No. 4,968,483 is employed to carry out the method of the invention. The disclosure of U.S. Pat. No. 4,968,483 is incorporated herein in its entirety by reference.

In a preferred aspect of the invention, a method of increasing the nitric oxide concentration in the blood of a human is provided, which comprises:

(a) contacting from about 0.01 ml to about 400 ml of blood with nitric oxide concentration-increasing effective amount of ozone gas supplied in a concentration from about 5 µg/ml to about 50 µg/ml of ozone gas in an oxygen containing gas stream and ultraviolet radiation having a wavelength of about 253.7 nm, while maintaining the blood at a temperature of from about 37° C. to about 43° C.; and (b) administering the treated blood to a human.

The invention also contemplates a method of treating a condition in a human, which comprises:

(a) contacting from about 0.01 ml to about 400 ml of blood with a nitric oxide concentration-increasing effective amount of ozone gas and ultraviolet radiation; and (b) administering the treated blood to a human.

The useful and preferred ranges of ozone concentration, ultraviolet wavelength, temperature, and other parameters of the method of treatment are the same as described above with regard to the method of increasing nitric oxide blood concentration.

Those skilled in the art will appreciate that the method of increasing nitric oxide blood concentration provided by the invention will have therapeutic utility for treating a wide range of disease states which may be benefitted by increasing the levels of nitric oxide in the blood.

The term "treating" as used herein refers to the alleviation or prevention of a particular disorder. In the case of traumatic conditions such as stroke, preventative treatment is obviously preferred.

The following diseases are illustrative of known conditions which are potentially treatable according to the inventive method: high blood pressure; neurological conditions such as depression; tumors; bacterial, viral, protozoal, and fungal infections and impotence. This list is merely illustrative; those of ordinary skill in the art will appreciate that other disease states benefitted by increasing the concentration of nitric oxide in the blood may be treated with the inventive technique.

The treatment of peripheral vascular disease with UV/ozone gas is described in grandparent application Ser. No. 07/832,798 filed on Feb. 7, 1992, which is now abandoned. The vascular bed of the body is considered to be a single system, and hence any treatment for peripheral vascular disease will be effective for similar pathologies found in all other parts of vascular system e.g. the heart (cardiovascular disease) and the brain (cerebrovascular disease, a cause of stroke). Peripheral vascular disease (PVD) is thought to be associated with a reduction of endothelial-derived relaxing factor (EDRF), low levels of which lead to a concentration of the smooth muscle of blood vessels, and hence a reduction in the diameter of the lumen of the vessel and a reduction in blood flow. The major naturally occurring EDRF is nitric oxide. In addition, nitric oxide stabilizes blood platelets, reducing their aggregation. An increase in EDRF (nitric oxide) levels, therefore, has a double beneficial effect on the circulatory system: it inhibits aggregation of platelets, making the blood more fluid, and it enlarges the diameter of the vessels, improving the flow. The reverse, a reduction in nitric oxide levels, may be present in peripheral vascular disease, and the other conditions described above which may be benefitted by increasing the blood concentration of nitric oxide.

As illustrated in the examples below, the method of the invention is believed to increase nitric oxide levels in the blood, which may explain the mode of action in the inventive treatment of peripheral vascular disease and other conditions associated with blood platelet aggregation and nitric oxide deficiency.

The following examples are given to illustrate the invention but are not deemed to be limiting thereof.

EXAMPLE 1

INHIBITION OF BLOOD PLATELET AGGREGATION

The following experiment was conducted to study the effects of ozone/ultraviolet light treatment on blood platelet activity.

EXPERIMENTAL PROCEDURE

Samples (20 ml) of peripheral blood were taken from 10 individuals for 13 separate experiments. Each sample was divided into two aliquots. The first aliquot was treated according to the inventive technique, as follows:

The 10 ml aliquot was treated in vitro for three minutes with ozone gas (variable ozone concentration of 5–50 µg/ml) and ultraviolet light (253.7 nm), at a temperature of 42.5° C. An apparatus as disclosed in U.S. Pat. No. 4,968,483 was utilized to carry out the treatment of the blood sample.

The second 10 ml aliquot from each sample served as an untreated control.

Platelets were isolated from the control or treated samples by centrifugation, and their ability to aggregate in response to different concentrations of ADP (a natural platelet stimulator) was measured in an aggregometer. A sample of both ozone-treated and untreated blood was used for quantitation of platelet numbers, using a Coulter counter. In some of the experiments described below, aliquots of the blood were treated with different concentrations of ozone. In other experiments performed, the blood was treated in the presence and absence of UV-light irradiation.

In the reported data, control samples were assigned a number of 100 for platelet aggregation and platelet aggregation in the ozone-treated blood was expressed as a percentage of this 100% aggregation in the same person untreated control blood.

RESULTS

As shown in Table 1, the results of the experiments indicate that treatment of blood with ozone and ultraviolet light according to the invention inhibits the aggregation of blood platelets. Furthermore, there is an indication that this inhibition is dose related to the ozone concentration (see Table 2).

THE EFFECT OF HIGH LEVELS OF OZONE ON ADP-STIMULATED BLOOD PLATELETS

High levels of ozone (between 35 and 50 μg/ml) caused a measurable inhibition of ADP-induced platelet aggregation (arbitrarily taken as 33.3% inhibition) in 11 of the 13 experiments (8 of the 10 individuals). Taking all the data on all 10 individuals, the mean inhibition of platelet aggregation was 49.2+/−27.8% (mean+/−sd). There was no significant difference between the inhibitory effects on blood taken from males and females (mean inhibition 48.1% and 50.7%, respectively).

This inhibition appears to relate to the concentration of ADP (aggregation stimulator) over the concentration range of 0.01–0.1 mM ADP, with lower inhibition at higher concentrations of platelet agonist. However, this relationship did not hold at higher ADP concentrations (Table 1) and could be spurious, although the level of inhibition at 0.01 mM ADP is significantly greater than at 0.1 mM ADP (71% vs. 95%, p<0.02).

TABLE 1

The effect of high levels of ozone on the aggregation of human blood platelets in the presence of varying concentration of ADP.

| Date (Individual) | Concentration of ozone (μg/ml) | Concentration of ADP (mM) | Percent Inhibition of Aggregation | Platelet Count Before Ozone | Platelet Count After Ozone |
|---|---|---|---|---|---|
| 21.11.91 (F1) | 50 | 10 | 100 | (i.e. no aggregation) | |
| 27.11.91 (M1) | 50 | 5 | 83.3 | | |
| | | 10 | 71.4 | | |
| | | 30 | 75.0 | | |
| 2.12.91 (F2) | 50 | 10 | 0 | (i.e. aggregation as with control) | |
| | | 30 | 10.0 | | |
| | | 100 | 27.3 | | |
| 3.12.91 (M2) | 50 | 0.5 | 67.1 | | |
| | | 1 | 57.1 | | |
| | | 5 | 50.0 | | |
| | | 30 | 88.1 | | |
| 6.12.91 (M3) | 50 | 0.1 | 0 | 34 | 49 |
| | | 0.1 | 6.2 | | |
| | | 0.5 | 4.0 | | |
| | | 0.5 | 0 | | |
| 11.12.91 (M4) | 50 | 0.05 | 67.0 | 56 | 93 |
| | | 0.1 | 62.4 | | |
| | | 1.0 | 74.3 | | |
| | | 10.0 | 50.0 | | |
| 12.12.91 (M5) | 50 | 0.01 | 67.0 | 51 | 121 |
| | | 0.1 | 7.1 | | |
| | | 1.0 | 35.7 | | |
| 13.12.91 (F1) | 50 | 0.01 | 63.4 | 33 | 87 |
| | | 0.05 | 22.7 | | |
| | | 0.1 | 30.4 | | |
| | | 0.5 | 15.4 | | |
| | | 1.0 | 20.8 | | |
| | | 5.0 | 20.0 | | |
| | | 10.0 | 27.6 | | |
| 9.01.92 (M6) | 50 | 0.01 | 34.2 | 34 | 40 |
| | | 0.05 | 31.0 | | |
| | | 0.1 | 9.8 | | |
| | | 0.5 | 15.4 | | |
| | | 1.0 | 26.2 | | |
| | | 5.0 | 31.3 | | |
| 10.01.92 (F3) | 50 | 0.001 | 71.4 | 49 | 64 |
| | | 0.005 | 37.5 | | |
| | | 0.01 | 69.8 | | |
| | | 0.05 | 33.8 | | |
| | | 0.1 | 31.2 | | |
| | | 0.5 | 10.1 | | |
| | | 1.0 | 21.8 | | |

-continued

| | | | | | |
|---|---|---|---|---|---|
| 13.01.92 (F4) | 50 | 0.005 | 100 | 49 | 52 |
| | | 0.01 | 100 | | |
| | | 0.05 | 95.2 | | |
| | | 0.1 | 92.9 | | |
| | | 0.5 | 95.8 | | |
| | | 1.0 | 91.6 | | |
| | | 5.0 | 95.8 | | |
| | | 10.0 | 80.0 | | |
| 15.01.92 (F1) | 40 | 0.01 | 90.0 | 81 | 66 |
| | | 0.05 | 71.4 | | |
| | | 0.1 | 40.7 | | |
| | | 0.5 | 87.0 | | |
| | | 1.0 | 81.8 | | |
| | | 5.0 | 95.5 | | |
| | | 10.0 | 85.2 | | |
| | | 50.0 | 84.0 | | |
| | | 100.0 | 79.1 | | |
| 21.01.92 (M2) | 35 | 0.01 | 67.1 | 68 | 79 |

The following is a summary of the data set forth in Table 1.

| ADP mM | 0.01 | 0.05 | 0.10 | 0.50 | 1.00 | 5.00 | 10.0 |
|---|---|---|---|---|---|---|---|
| % Inhibition of Aggregation | 70.8 +/− 20.9 | 53.5 +/ 26.1 | 34.7 +/− 28.4 | 37.6 +/− 38.4 | 50.3 +/− 28.7 | 60.7 +/− 35.2 | 60.7 +/− 30.4 |
| N = | 6 | 6 | 8 | 7 | 7 | 4 | 4 |

THE EFFECT OF HIGH LEVELS OF OZONE ON TOTAL WHOLE BLOODPLATELET COUNTS

As any apparent reduction in platelet aggregation following ozone treatment of whole blood could be caused by a loss of platelets from the blood during treatment, total whole platelet counts were performed on the treated and untreated whole blood samples in 9 experiments on blood from 8 individuals. Overall, the platelet count was 115.5+/−59.8% of the untreated level following ozonization (range 82–264%).

Thus, the total platelet counts before and after ozone/UV treatment do not indicate a major loss of platelets from the blood as a result of ozonization.

THE EFFECT OF DIFFERENT CONCENTRATIONS OF OZONE ON THE INHIBITION OF AGGREGATION OF HUMAN BLOOD PLATELETS STIMULATED WITH ADP

Three different concentrations of ozone (5, 25, and 50 $\mu$g/ml) were used at a range of ADP concentrations in 4 experiments on 4 different individuals. Bulking the data for different ozone concentrations from each individual and calculating the mean for the data from the 4 experiments indicated that there was some dose response relationship between the concentration of ozone used and the inhibition of platelet aggregation (See Table 2).

Although overall these differences were not significant, in two of the four individuals there was a significantly greater inhibitory effect of ozone at 50 $\mu$g/ml then at 5 $\mu$g/ml (See Table 3).

TABLE 2

The effect of different concentrations of ozone on inhibition of platelet aggregation in the presence of ADP.

| Date (Individual) | Concentration of Ozone ($\mu$g/ml) | Concentration of ADP (mM) | Percent Inhibition of Aggregation | Platelet Count Before Ozone | After Ozone |
|---|---|---|---|---|---|
| 3.12.9 | 15 | 0.1 | 27.3 | | |
| (M2) | 25 | 0.1 | 100 | | |
| | 5 | 0.5 | 0 | | |
| | 25 | 0.5 | | | |
| | 50 | 0.5 | 67.1 | | |
| | 5 | 1.0 | 0 | | |
| | 25 | 1.0 | 28.6 | | |
| | 50 | 1.0 | 57.1 | | |
| | 5 | 5.0 | 0 | | |
| | 25 | 5.0 | 25.0 | | |
| | 50 | 5.0 | 50.0 | | |
| | 5 | 30.0 | 50.0 | | |
| | 25 | 30.0 | 62.0 | | |
| | 50 | 30.0 | 88.1 | | |

TABLE 2-continued

The effect of different concentrations of ozone on inhibition of platelet aggregation in the presence of ADP.

| | | | | | |
|---|---|---|---|---|---|
| 9.01.92 | 5 | 0.01 | 20.1 | 34 | 43 |
| (M6) | 25 | 0.01 | 28.9 | | 45 |
| | 50 | 0.01 | 34.2 | | 40 |
| | 5 | 0.05 | 0 | | |
| | 25 | 0.05 | 5.2 | | |
| | 50 | 0.05 | 31.0 | | |
| | 5 | 0.1 | 9.8 | | |
| | 25 | 0.1 | 1.4 | | |
| | 50 | 0.1 | 9.8 | | |
| | 5 | 0.5 | 0 | | |
| | 25 | 0.5 | 15.0 | | |
| | 50 | 0.5 | 15.4 | | |
| | 5 | 1.0 | 22.5 | | |
| | 25 | 1.0 | 13.7 | | |
| | 50 | 1.0 | 26.2 | | |
| | 5 | 5.0 | 0 | | |
| | 25 | 5.0 | 17.8 | | |
| | 50 | 5.0 | 31.5 | | |
| 10.01.92 | 5 | 0.001 | 57.1 | 49 | 73 |
| (F3) | 25 | 0.001 | 85.7 | | 90 |
| | 50 | 0.001 | 71.4 | | 64 |
| | 5 | 0.005 | 37.5 | | |
| | 25 | 0.005 | 80.0 | | |
| | 50 | 0.005 | 37.5 | | |
| | 5 | 0.01 | 66.4 | | |
| | 25 | 0.01 | 83.2 | | |
| | 50 | 0.01 | 69.8 | | |
| | 5 | 0.05 | 44.9 | | |
| | 25 | 0.05 | 66.9 | | |
| | 50 | 0.05 | 33.8 | | |
| | 5 | 0.1 | 29.3 | | |
| | 25 | 0.1 | 61.0 | | |
| | 50 | 0.1 | 31.2 | | |
| | 5 | 0.5 | 39.4 | | |
| | 25 | 0.5 | 54.5 | | |
| | 50 | 0.5 | 10.1 | | |
| | 5 | 1.0 | 21.8 | | |
| | 25 | 1.0 | 52.9 | | |
| | 50 | 1.0 | 21.8 | | |
| 13.01.92 | 5 | 0.005 | 100 | 49 | 60 |
| (F4) | 25 | 0.005 | 100 | | 85 |
| | 50 | 0.005 | 100 | | 52 |
| | 5 | 0.01 | 100 | | |
| | 25 | 0.01 | 87.5 | | |
| | 50 | 0.01 | 100 | | |
| | 5 | 0.05 | 84.8 | | |
| | 25 | 0.05 | 97.1 | | |
| | 50 | 0.05 | 95.2 | | |
| | 5 | 0.1 | 82.9 | | |
| | 25 | 0.1 | 91.4 | | |
| | 50 | 0.1 | 92.9 | | |
| | 5 | 0.5 | 83.3 | | |
| | 25 | 0.5 | 95.8 | | |
| | 50 | 0.5 | 95.8 | | |
| | 5 | 1.0 | 83.2 | | |
| | 25 | 1.0 | 89.5 | | |
| | 50 | 1.0 | 91.6 | | |
| | 5 | 5.0 | 79.2 | | |
| | 25 | 5.0 | 91.7 | | |
| | 50 | 5.0 | 95.8 | | |
| | 5 | 10.0 | 85.3 | | |
| | 25 | 10.0 | 80.0 | | |
| | 50 | 10.0 | 80.0 | | |

The following is a summary of the data set forth in Table 2:

| Concentration of ozone ($\mu$g/ml) | 5 | 25 | 50 |
|---|---|---|---|
| Platelet Aggregation (%) (mean +/− sd, n = 4) | 38.5 +/− 30.9 | 56.5 +/− 29.4 | 55.9 +/− 26.4 |

TABLE 3

The effect of different concentrations of ozone on
inhibition of platelet aggregation in two individuals.

| Concentration of ozone (µg/ml) | 5 | 25 | 50 |
|---|---|---|---|
| Platelet aggregation M2 (%) | 15.5 +/− 20.2 | 53.9 +/− 30.0 | 65.6 +/− 14.4 |
| Difference from 5 µg/ml | | ns | p < 0.01 |
| Platelet aggregation M6 (%) | 8.7 +/− 9.6 | 11.2 +/− 10.2 | 24.7 +/− 9.0 |
| Difference from 5 µg/ml | | ns | p < 0.02 | ns = not significant

THE EFFECT OF UV LIGHT ON THE RESPONSE OF PLATELETS TO OZONE

The effect of ozone on the aggregation of human blood platelets was investigated at different concentrations of ADP, in the presence or absence of UV light. The results, shown in Table 4, indicate that, although there may be some platelet aggregation-inhibitory response to ozone alone, this is nearly always greater in the presence of UV light and the effect of UV light was highly significant (p<0.001) in this single experiment. This result was also repeated in a second experiment, using a single concentration of ADP (0.01 mM). The results of this second experiment are set forth in Table 5.

TABLE 4

The effect of UV light on the inhibition of ADP-
induced platelet aggregation by ozone at a concentration of
40 µg/ml. (Experiment date 15.01.92, individual F1).

| | Inhibition of Platelet Aggregation (%) | |
|---|---|---|
| Concentration ADP (mM) | +UV | −UV |
| 0.01 | 90.0 | 60.0 |
| 0.05 | 71.4 | 0 |
| 0.1 | 40.7 | 40.7 |
| 0.5 | 87.0 | 0 |
| 1.0 | 81.8 | 0 |
| 5.0 | 95.5 | 19.4 |
| 10.0 | 85.2 | 18.5 |
| 50.0 | 84.0 | 16.0 |
| 100.0 | 79.1 | 4.2 |
| Mean +/− sd | 79.4 +/− 15.1 | 17.6 +/− 19.6 (p < 0.001) |

TABLE 5

The effect of UV light on platelet aggregation
induced by ADP (0.01 mM) in the presence or absence of ozone.
(Experiment date 21.01.92, individual M2)
Percent Inhibition of Platelet Aggregation

| Ozone 35 µg/ml + UV | Ozone 35 µg/ml − UV | No ozone, UV alone |
|---|---|---|
| 83.4% | 11.2% | 0% |

In summary, the results of Example 1 indicate that the in vitro treatment of an aliquot of blood with ozone gas and ultraviolet light inhibits the aggregation of blood platelets. This platelet inhibition has been found to be dose related to the ozone concentration. Further, platelet inhibition was found to critically depend on the combined treatment of ultraviolet light and ozone gas, as evidenced in Tables 4 and 5. Treatment with ozone gas alone resulted in minimal inhibition of platelet aggregation, while treatment with ultraviolet light alone produced no inhibition of platelet aggregation.

EXAMPLE 2

MEASUREMENT OF NITRIC OXIDE

In order to elucidate the mechanism whereby ozonization/UV light affects the aggregation of platelets in treated blood, the concentration of certain oxidized forms of nitrogen were measured.

The direct measurement of nitric oxide is difficult to achieve. However, nitric oxide is an intermediate in an metabolic pathway in which arginine is converted to citrulline, which is accompanied by the production of other stable end-products including thiol-nitric oxide (nitrite) complexes, metal-thiol-nitric oxide (nitrite) complexes and oxidized forms thereof i.e. nitrates.

Accordingly, the nitric oxide content for several samples of blood treated with ultraviolet light and ozone gas according to Example 1 were indirectly determined by measuring the combined nitrite plus nitrite concentrations in the samples before and after treatment with ozone/UV light, after converting nitrate to nitrite.

The results show that there is a small increase in nitrate plus nitrite concentrations after treatment according to the invention. This increase was consistently found in samples treated with ozone gas/UV light. Thus, nitric oxide levels appear to be enhanced by the treatment with ozone gas/UV light, and this appears to be part of the mode of action by which an inhibition of blood platelet aggregation is achieved by the invention. This therapeutic effect is consistent with the etiology of peripheral vascular disease described above.

CONCLUSIONS

The data of Examples 1 and 2 suggest that the treatment of blood with ozone gas and ultraviolet light according to the invention is actually inducing an inhibition of platelet aggregation for the following reasons:

1. The inhibitory effect is at least partially dependent on the concentration of ADP, ozone being more inhibitory at lower ADP concentrations. This may be interpreted as the higher agonist concentrations partially overcoming the inhibitory effect of ozone by "hyperstimulating" the platelets. This suggests that the inhibition is at least partially reversible, and is probably not acting by destroying the platelet's ability to aggregate.

2. The inhibitory effect appears to be dose related to ozone concentration, with higher concentrations of ozone resulting in a greater inhibition of platelet aggregation.

3. The inhibitory effect is UV-dependent, suggesting that this is not a non-specific toxic effect caused by the oxidative capacity of the ozone gas.

EXAMPLE 3

Venous blood (20 ml), taken from 13 healthy non-smoking volunteers, 6 females and 7 males, age 20–50 years, was collected into sodium citrate anticoagulant. None of the volunteers had taken any medication for at least one week prior to the investigation. The blood was divided into two 10 ml aliquots. One aliquot was treated with ozone/UV as described below, the other was an untreated control sample.

OZONE TREATMENT OF BLOOD SAMPLES

Blood was treated according to the invention with different concentrations of ozone using a device similar to that described in U.S. Pat. No. 4,968,483. Ozone in medical oxygen was bubbled through the blood sample at a rate of 0.3 1/min for a fixed period of about 3 minutes. The blood was heated to a temperature of 42.5° C. and exposed to ultraviolet light at a wavelength of 253.7 nm. The concentration of ozone in the oxygen carrier was variable between about 5 and 50 µg/ml, and was measured using an ozone monitor (Humares, Karlsruhe, Germany).

PLATELET AGGREGATION STUDIES

Platelet aggregation was measured essentially by the end point turbidimetric method of Born.

Platelet rich plasma (PRP) was prepared by centrifuging 10 ml of blood (either ozone-treated or untreated control blood) at room temperature for 20 minutes at 200 xg. Four ml of PRP was diluted by the addition of 1.0 ml of phosphate-buffered saline.

Diluted PRP (0.225 ml) was placed in an aggregometer cuvette containing a small magnetic stirrer bar (aggregometer model 1002, ADG Instruments Ltd., Codicote, Herts., U.K.) and equilibrated at 37° C. After stirring was commenced, 0.025 ml of agonist (either ADP—ADP platelet aggregation reaction or collagen—collagen platelet aggregation reagent; both from Sigma Chemical Co., Poole, Dorset, U.K.) was added to the final concentrations indicated in the results section below. The maximum change in light transmission was measured. Platelet aggregation in the ozone-treated samples was expressed as a percent of the aggregation in the control samples for each individual experimental condition.

Blood platelet counts were performed on whole blood, using a Coulter counter, provided by the Department of Hematology, Northern General Hospital, Sheffield, U.K.

RESULTS

Following treatment of whole blood with 35–50 µg/ml of ozone in oxygen at a flow rate of 0.3 1/min for 3 min (total mass of ozone reacted: 31.5–45 mg) with exposure to UV, there was an apparent overall increase in the platelet count, to 1461/57% (mean+/−standard deviation, range 81–202%) of the control value in the 12 individuals investigated. This suggests that, under the conditions used in these experiments, the treatment of whole blood with ozone does not destroy the blood platelets. Furthermore, following visual assessment, no marked hemolysis was observed in the treated blood compared with the control blood samples, indicating that the treatment regime had little effect on erythrocyte integrity.

Platelets from blood treated with a concentration of 35–50 µg/ml ozone as above showed a reduction in their ability to aggregate in response to ADP (0.001–100 mmol/l concentrations). The overall inhibition of aggregation was 53.1+/−31.1% (mean+/−standard deviation, n=13). The inhibition was variable between individuals, ranging from 2.6% to 100%.

This inhibitory effect of ozone/UV treatment was dependant on the concentration of ADP, showing a higher level of inhibition of platelet aggregation at low concentrations of ADP (See Table 6). The inhibitory effect at 0.01 mmol/l ADP was significantly greater (p<0.02) than at 0.1 mmol/l of this agonist (See Table 6).

With collagen as an inducer of platelet aggregation, platelets treated with 35–50 µg/ml ozone in oxygen also showed a high level of inhibition of aggregation: 74.2+/−43.3% with 1 mg/mol collagen and 76.4+/−25.2% with 10 mg/ml collagen (n=5).

A reduction in the concentration of ozone in the oxygen bubbled through the blood sample resulted in a reduction in the effect of treatment on the inhibition of platelet aggregation. This difference was significant in individual responses to treatment, although the overall mean values of the four individuals investigated were not significantly different (See Table 7).

TABLE 6

The effect of different concentrations of the platelet agonist ADP on the inhibition of ADP-induced platelet aggregation by treatment of blood in vitro with ozone at a concentration of 50 µg/ml in oxygen and UV irradiation.

| Subject | Conc. ADP (mmol/l) | Percent Inhibition of Platelet Aggregation |
|---|---|---|
| Male 1 | 0.5 | 67.1 |
|  | 1.0 | 57.1 |
|  | 5.0 | 50.0 |
| Female 1 | 0.001 | 71.4 |
|  | 0.01 | 69.8 |
|  | 0.1 | 31.2 |
|  | 1.0 | 21.8 |
| Female 2 | 0.01 | 63.4 |
|  | 0.1 | 30.4 |
|  | 1.0 | 20.8 |
| Mean | 0.01 | 70.8 +/− 20.9, n = 6 |
|  | 0.05 | 53.5 +/− 26.1, n = 6 |
|  | 0.1 | 34.7 +/−28.4, n = 8* |

*significantly different from 0.01 mmol/1, $p < 0.02$

TABLE 7

The effect of different concentrations of ozone on the inhibition of ADP-induced platelet aggregation by treatment of whole blood in vitro with ozone in oxygen and UV irradiation

| | Percent Inhibition of Platelet Aggregation | | |
|---|---|---|---|
| Subject | 5 µg/ml Ozone | 25 µg/ml Ozone | 50 µg/ml Ozone |
| Male 1 | 15.5 | 53.9 | 65.6** |
| Male 2 | 8.7 | 11.2 | 24.7* |
| Mean (n = 4) | 38.5 | 56.5 | 55.9 |
| sd | 30.9 | 29.4 | 26.4 |

**significant at $p < 0.01$
*significant at $p < 0.02$

EXAMPLE 4

THE EFFECT OF UV/OZONE TREATMENT OF BLOOD IN VITRO ON THE PLASMA NITRIC OXIDE CONCENTRATION

EXPERIMENTAL OUTLINE

Blood (10 ml), anticoagulated with sodium citrate, from 14 normal healthy individuals, was treated with UV/ozone gas as described in Example 3, with oxygen containing ozone at a concentration of 20–50 µg/ml. Control blood from each individual was not treated. After removal of the cellular components of the blood by centrifugation at 15 000×g for 30 seconds, the plasma was stored at −20° C.

Nitric oxide, produced metabolically from L-arginine, is unstable and reacts with oxygen to form nitrate and nitrite. Total nitrate plus nitrite was measured after conversion of nitrate to nitrite using a cadmium catalyst. Nitrite was measured colorimetrically using the Griess reagent by a method based on that published by Green, Wagner, Glogowski, Skipper, Wishnok & Tannebaum in 1982 (*Analytical Biochemistry,* Vol. 126, pages 131–138). All treated and control samples were measured in a single assay run.

RESULTS

The actual values of nitrite concentration varied widely between individuals, ranging from 0.6–27.6 μmol/l. To enable comparisons between individuals, the concentration of nitrite in the ozone-treated sample was expressed as a percent of the concentration in the corresponding untreated control. A summary of the results is as follows:

| Individual No. | Percent of Nitrite in Ozonated Sample Compared to Control |
| --- | --- |
| 1 | 28.0 |
| 2 | 36.7 |
| 3 | 48.9 |
| 4 | 76.4 |
| 5 | 110.0 |
| 6 | 133.3 |
| 7 | 157.6 |
| 8 | 162.9 |
| 9 | 175.8 |
| 10 | 350.0 |
| 11 | 845.5 |
| 12 | 985.7 |
| 13 | 2075.0 |
| 14 | 3067.0 |
| Arithmetic Mean | 589.5% |

These values do not form a normal distribution. However, an approximate normal distribution can be attained after logarithmic transformation of the data. Following logarithmic transformation, the level of nitrite in the UV/ozone-treated blood samples is significantly greater than in the untreated samples ($p<001$).

INHIBITION STUDIES

Nitric oxide inhibits platelet aggregation—this is one of its physiological activities. It is known that the effect of nitric oxide on platelets can be inhibited by free oxyhemoglobin (Salvemini, Radziszewski, Korbut & Vane, *Br. J. Pharmacol.;* Vol. 101, pages 991–995, 1990). We therefore investigated the effect of oxyhemoglobin on the platelet aggregation inhibitory action of treatment of whole blood with UV/ozone gas.

EXPERIMENTAL OUTLINE

Platelet rich plasma was prepared from whole blood, either treated with UV/ozone or untreated (control), by centrifugation at 200×g for 20 minutes at room temperature. Platelet aggregation in response to ADP, collagen or thrombin as stimulators was measured in an aggregometer. Oxyhemoglobin was added to the platelet rich plasma subsequent to ozonization and before measuring platelet aggregation activity. If treatment of blood with UV/ozone to inhibit platelet aggregation is acting via a nitric oxide-mediated mechanism, then the addition of oxyhemoglobin should prevent the inhibition of platelet aggregation caused by UV/ozonization. The results are set forth in Table 8 below.

TABLE 8

| | | PERCENT INHIBITION OF PLATELET AGGREGATION AFTER OZONE/UV TREATMENT | |
| --- | --- | --- | --- |
| Subject | Platelet Agonist | No Hb | 10 μmol/l Hb |
| Female a | Thrombin 100 iu | 23 | 4 |
| Female b | Thrombin 100 iu | 57 | 0 |
| | Thrombin 10 iu | 97 | 57 |
| | ADP 1 mmol/l | 36 | 0 |
| Male a | Thrombin 10 iu | 80 | 79 |
| | Collagen 1 mg/ml | 95 | 80 |
| | ADP 1 mmol/l | 16 | 0 |
| | ADP 0.1 mmol/l | 26 | 9 |

Although rather variable, two of the three subjects showed consistent reductions of post-UV ozone therapy platelet aggregation inhibition in the presence of haemoglobin, and the third subject showed some reduction with 3 of the 4 conditions of aggregation used. The overall means of platelet aggregation were 54% without haemoglobin and 29% in the presence of this inhibitor of nitric oxide activity.

CONCLUSIONS

The above data show that ozonization of blood raises the level of nitrite (the stable metabolite of nitric oxide), and that the inhibition of platelet aggregation caused by ozonization of blood can be reversed by haemoglobin, an inhibitor of nitric oxide activity. Taken together, these data strongly suggest that the treatment of blood with UV/ozone according to the invention increases the in vivo blood levels of nitric oxide, and inhibits the aggregation of platelets via a nitric oxide mediated mechanism.

EXAMPLE 5

IN VIVO STUDIES

The effect of the administration of UV/ozone treated blood on patients with vascular disease.

INTRODUCTION

It is known that in vivo nitric oxide has an effect on blood vessels, causing a relaxation of the muscle layer of the vessel wall resulting in vasodilation and an increase in the flow of blood through the vessel. Thus, evidence for an increase in nitric oxide production may be obtained from measurements of blood flow. However, the flow of blood through the vessels is controlled by complex interacting mechanisms and the measurement of basal blood flow will not reproducibly reflect effects of nitric oxide alone. Therefore, in order to examine the effect of nitric oxide, blood flow is measured in response to stimulating drugs which are known to be mediated via nitric oxide production. One such drug is acetyl choline which is known to stimulate the production of nitric oxide by the cells of the endothelium (blood vessel lining) thereby causing vasodilation and an increase in blood flow.

EXPERIMENTAL OUTLINE

Blood (10 mL), anticoagulated with sodium citrate, was obtained from patients with a peripheral vascular disease and was treated in vitro with oxygen containing ozone at a concentration of 15 μg ozone/mL oxygen, UV light at a wavelength of 253.7 nm at a temperature of 42.5° C. for three minutes utilizing an apparatus as disclosed in U.S. Pat.

No. 4,968,483. Following treatment, the blood was returned to the patient by intramuscular injection in the gluteal muscle. Each patient received 10 such individual treatments over a period of 2–4 weeks. A total of four patients was investigated.

Before and after the course of treatments described in the preceding paragraph, blood flow in the superficial blood vessels of the forearm were measured by a method combining laser Doppler blood flow measurements with the iontophoretic introduction of acetyl choline, using a commercially available device (DRT4 laser Doppler perfusion and temperature monitor and MIC 1 iontophoresis controller, from Moore Instruments Ltd., Axminster, Devonshire, UK). The blood flow resulting from the introduction of up to 36.2 $\mu$g of acetyl choline was measured. In each case, this dose of acetyl choline gave a maximal response in terms of blood flow. The blood flow in response to this dose of acetyl choline was measured before and after the course of treatment with the in vitro treated blood in each patient, the results being expressed in units of blood flow.

RESULTS

Before a course of treatment with the in vitro treated blood, the average blood flow in response to acetyl choline was 186.9+/−34.4 units of blood flow (mean+/−standard deviation). Following the course of 10 treatments as described above, the average blood flow in response to acetyl choline was 261.1+/−106.0 units of blood flow (mean+/−standard deviation). Thus, following the course of treatment, the blood flow in response to acetyl choline increased by an average of 39.7%.

CONCLUSION

These results indicate that the blood flow in response to acetyl choline is increased after a course of treatment with in vitro treated blood. It is known that acetyl choline increases blood flow via nitric oxide generated using the intermediary effects of the endothelium. Hence, this provides evidence that there is a greater level of available nitric oxide in the blood vessel following treatment of a patient with the blood treated by the method of the invention, probably due to the effects of the re-injected treated blood (or some component of it) on the endothelium lining the blood vessels. Thus, not only does the treated blood aliquot of the present invention itself provide enhanced nitric oxide levels to the blood, for beneficial purposes, the treated aliquot of blood, after re-introduction into the blood stream of the human patient, itself stimulates generation of extra nitric oxide in the blood, by stimulation of endothelial action.

What is claimed is:

1. A method of inducing relaxation of the smooth muscle of blood vessels of a human patient to effect enlargement in the diameter of said blood vessels, which comprises the successive steps of:
   (a) extracting an aliquot of blood, of volume from about 0.01 ml to about 400 ml, from the human patient;
   (b) in vitro contacting the extracted aliquot of human blood with a nitric oxide concentration-increasing effective amount of ozone gas as an oxygen/ozone gas stream having an ozone concentration of from 0.5 $\mu$g/ml to about 100 $\mu$g/ml, and ultraviolet radiation, for a period of time from about 0.5–10 minutes and at a temperature, in the range 0°–56° C., which does not cause marked hemolysis in the blood aliquot or does not cause a major loss of platelets from the blood, to produce an aliquot of treated blood; and
   (c) increasing the nitric oxide concentration in the blood of said patient by administering said treated blood to the same human patient.

2. The method of claim 1, wherein the ultraviolet radiation has a wavelength of about 253.7 nm.

3. The method of claim 1, wherein the aliquot of human blood in step (a) comprises about 10 ml of blood.

4. The method of claim 1, wherein the blood aliquot is contacted with the oxygen/ozone gas stream and ultraviolet radiation for a period of about 3 minutes.

5. The method of claim 1, wherein the treated blood is administered to the human by a method selected from the group consisting of inter-arterial injection, intramuscular injection, intravenous injection, subcutaneous injection, and intraperitoneal injection.

6. The method of claim 1 wherein the aliquot of blood in Step (a) has a volume from about 1–50 ml.

7. The method of claim 6 wherein the blood aliquot is maintained at a temperature of from about 37°–43° C. during the contact with ozone gas and ultraviolet radiation.

8. The method of claim 1, wherein the ultraviolet radiation is from a UV-C source of ultraviolet radiation.

9. A method of alleviating the symptoms of peripheral vascular disease in a human patient suffering therefrom, by increasing the nitric oxide concentration in the human patient's blood, which comprises the steps of:
   (a) extracting an aliquot of blood, of volume about 0.1–200 ml, from the human patient;
   (b) in vitro contacting the extracted aliquot of blood with a nitric oxide concentration-increasing effective amount of ozone gas, as a mixture of ozone in an oxygen-ozone gas stream having an ozone concentration of from about 0.5 $\mu$g/ml to about 100 $\mu$g/ml, while the aliquot of blood is simultaneously being subjected to ultraviolet radiation, for a period of time from about 0.5–10 minutes and at a temperature in the range of 0°–56° C. which does not cause marked hemolysis or major loss of platelets in the blood aliquot; and
   (c) administering the treated aliquot of blood so obtained to said human patient so that stimulated leukocytes in said aliquot effect an increase in nitric oxide concentration in the human patient's blood.

10. The method of claim 9 wherein the blood aliquot is maintained at a temperature of from about 37°–43° C. during the contact with ozone and subjection to ultraviolet radiation.

11. A method of increasing the nitric oxide concentration in the blood of a human patient which comprises:
   (a) extracting an aliquot of blood, of volume from about 0.01 ml to about 400 ml, from a human patient;
   (b) in vitro contacting the extracted aliquot of human blood with a nitric oxide increasing amount of ozone gas and ultraviolet radiation for a period of time from about 0.5–10 minutes and at a temperature, in the range of 0–56° C., which does not cause a marked hemolysis in the blood aliquot or does not cause a major loss of platelets from the blood, to produce an aliquot of treated blood;
   (c) monitoring the increase in nitric oxide concentration in at least a portion of the aliquot of treated blood; and
   (d) readministering at least a portion of the treated blood aliquot with increased nitric oxide concentration to the same human patient.

12. The method of claim 11 wherein the ozone gas is contacted with a blood aliquot as a mixture of ozone in an oxygen-ozone gas stream having an ozone concentration of from 0.5 $\mu$g/ml to about 100 $\mu$g/ml.

* * * * *